United States Patent
Lee et al.

(10) Patent No.: US 10,390,800 B2
(45) Date of Patent: Aug. 27, 2019

(54) ULTRASOUND DIAGNOSIS METHOD AND ULTRASOUND DIAGNOSIS APPARATUS

(71) Applicant: SAMSUNG MEDISON CO., LTD., Hongcheon-gu (KR)

(72) Inventors: Jin-Yong Lee, Hongcheon-gun (KR); Sung-wook Park, Hongcheon-gun (KR); Jin-ki Park, Hongcheon-gun (KR); Joo-hyun Song, Hongcheon-gun (KR); Bong-heon Lee, Hongcheon-gun (KR); Hyuk-jae Chang, Seoul (KR); Nam-sik Chung, Seoul (KR); Geu-ru Hong, Seoul (KR); Jong-hwa Kim, Seoul (KR); Ji-hyun Yoon, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 959 days.

(21) Appl. No.: 14/938,246

(22) Filed: Nov. 11, 2015

(65) Prior Publication Data

US 2016/0128673 A1    May 12, 2016

(30) Foreign Application Priority Data

Nov. 11, 2014    (KR) .................. 10-2014-0156239

(51) Int. Cl.
*A61B 8/06*    (2006.01)
*A61B 8/08*    (2006.01)
*A61B 8/00*    (2006.01)

(52) U.S. Cl.
CPC .............. *A61B 8/5246* (2013.01); *A61B 8/08* (2013.01); *A61B 8/0883* (2013.01);
(Continued)

(58) Field of Classification Search
CPC .......... A61B 8/06; A61B 8/488; A61B 8/5426
See application file for complete search history.

(56) References Cited

U.S. PATENT DOCUMENTS 6,368,277 B1 *    4/2002    Mao .................... A61B 8/08
                                                          600/441
2005/0124881 A1    6/2005    Kanai et al.
(Continued)

FOREIGN PATENT DOCUMENTS

JP    2003-265483 A    9/2003
JP    2012-249967 A    12/2012
WO    2007/107926 A1    9/2007

*Primary Examiner* — Omkar A Deodhar
(74) *Attorney, Agent, or Firm* — Sughrue Mion, PLLC

(57) ABSTRACT

Provided are an ultrasound diagnosis apparatus and an ultrasound diagnosis method that provide to a user an ultrasound image which is easy to recognize. The ultrasound diagnosis apparatus includes a probe, an ultrasound transmitter configured to transmit ultrasound waves to an object by using the probe, an ultrasound receiver configured to generate ultrasound data based on reflection waves corresponding to the transmitted ultrasound waves, a bio-signal obtaining unit configured to obtain bio-signals that are periodically generated, a data processor configured to obtain first loop image data and second loop image data based on the ultrasound data, and an image generator configured to generate combined data by combining the first loop image data and the second loop image based on the bio-signals.

17 Claims, 11 Drawing Sheets

(52) U.S. Cl.
CPC ............ *A61B 8/4472* (2013.01); *A61B 8/463* (2013.01); *A61B 8/486* (2013.01); *A61B 8/488* (2013.01); *A61B 8/5207* (2013.01); *A61B 8/5223* (2013.01); *A61B 8/5253* (2013.01); *A61B 8/5284* (2013.01); *A61B 8/543* (2013.01)

(56) References Cited

U.S. PATENT DOCUMENTS

| | | | |
|---|---|---|---|
| 2012/0215110 A1 | 8/2012 | Wilkening et al. | |
| 2013/0006111 A1* | 1/2013 | Sasaki .................. | A61B 8/0891 600/441 |
| 2013/0165781 A1* | 6/2013 | Cardinale .............. | A61B 5/044 600/440 |

* cited by examiner

ULTRASOUND DIAGNOSIS METHOD AND ULTRASOUND DIAGNOSIS APPARATUS

RELATED APPLICATION

This application claims the benefit of Korean Patent Application No. 10-2014-0156239, filed on Nov. 11, 2014, in the Korean Intellectual Property Office, the disclosure of which is incorporated herein in its entirety by reference.

BACKGROUND

1. Field

One or more exemplary embodiments relate to an ultrasound diagnosis method and an ultrasound diagnosis apparatus.

2. Description of the Related Art

Ultrasound diagnosis apparatuses transmit ultrasound signals generated by transducers of a probe to an object and receive echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

There are cases in which there is a need to provide two or more Doppler spectrums or M mode images to a user, by using the ultrasound diagnosis apparatus. In this case, a method of providing the Doppler spectrums or the M mode images to the user, which enables the user to easily compare the two images, is needed.

SUMMARY

One or more exemplary embodiments include an ultrasound diagnosis apparatus and an ultrasound diagnosis method which provide an ultrasound image in a way in which a user can easily identify the ultrasound image.

Additional aspects will be set forth in part in the description which follows and, in part, will be apparent from the description, or may be learned by practice of the presented embodiments.

According to one or more exemplary embodiments, an ultrasound diagnosis apparatus includes a probe; an ultrasound transmitter configured to transmit ultrasound waves to an object by using the probe; an ultrasound receiver configured to generate ultrasound data based on reflection waves corresponding to the transmitted ultrasound waves; a bio-signal obtaining unit configured to obtain bio-signals that are periodically generated; a data processor configured to obtain first loop image data and second loop image data based on the ultrasound data; and an image generator configured to generate combined data by combining the first loop image data and the second loop image based on the bio-signals.

The ultrasound diagnosis apparatus may further include a display configured to display the first loop image data and the second loop image data simultaneously on a screen based on the combined data.

The image generator may configure a color map with respect to each of the first loop image data and the second loop image data, and the display may display the first loop image data and the second loop image data based on the configuration of the color map.

The image generator may determine at least one selected from a transparency, a sequential relationship, and the configuration of the color map, with respect to each of the first loop image data and the second loop image data.

The combined data generated by the image generator may include only data having a value that is equal to or higher than a reference level or only data having a value that is lower than the reference level, from among the first loop image data and the second loop image data.

The bio-signals may include electrocardiogram (ECG) information with respect to the object.

The image generator may determine a first characteristic point in the first loop image data, based on the bio-signals, may determine a second characteristic point corresponding to the first characteristic point, in the second loop image data, based on the bio-signals, and may combine the first loop image data and the second loop image data, based on a location of the first characteristic point and a location of the second characteristic point.

The first loop image data and the second loop image data may include at least one selected from Doppler spectrum data and M mode image data.

According to one or more exemplary embodiments, an ultrasound diagnosis method includes: transmitting ultrasound waves to an object by using a probe; generating ultrasound data based on reflection waves corresponding to the transmitted ultrasound waves; obtaining bio-signals that are periodically generated; obtaining first loop image data and second loop image data based on the ultrasound data; and generating combined data by combining the first loop image data and the second loop image data based on the bio-signals.

The ultrasound diagnosis method may further include displaying the first loop image data and the second loop image data simultaneously on a screen based on the combined data.

The generating of the combined data may include configuring a color map with respect to each of the first loop image data and the second loop image data, and the displaying of the first loop image data and the second loop image data may include displaying the first loop image data and the second loop image data based on the configuration of the color map.

The generating of the combined data may include determining at least one selected from a transparency, a sequential relationship, and the configuration of the color map, with respect to each of the first loop image data and the second loop image data.

The combined data may include only data having a value that is equal to or higher than a reference level or only data having a value that is equal to or lower than a reference level, from among the first loop image data and the second loop image data.

The obtaining of the bio-signals may include obtaining electrocardiogram (ECG) information with respect to the object.

The generating of the combined data may include determining a first characteristic point in the first loop image data, based on the bio-signals, determining a second characteristic point corresponding to the first characteristic point, in the second loop image data, based on the bio-signals, and combining the first loop image data and the second loop image data, based on a location of the first characteristic point and a location of the second characteristic point.

The first loop image data and the second loop image data may include at least one selected from Doppler spectrum data and M mode image data.

According to one or more exemplary embodiments, a non-transitory computer-readable recording medium has embodied thereon a computer program for executing the ultrasound diagnosis method.

BRIEF DESCRIPTION OF THE DRAWINGS

Embodiments of the invention now will be described more fully hereinafter with reference to the accompanying drawings, in which reference numerals denote structural elements.

DETAILED DESCRIPTION

Figure 1:
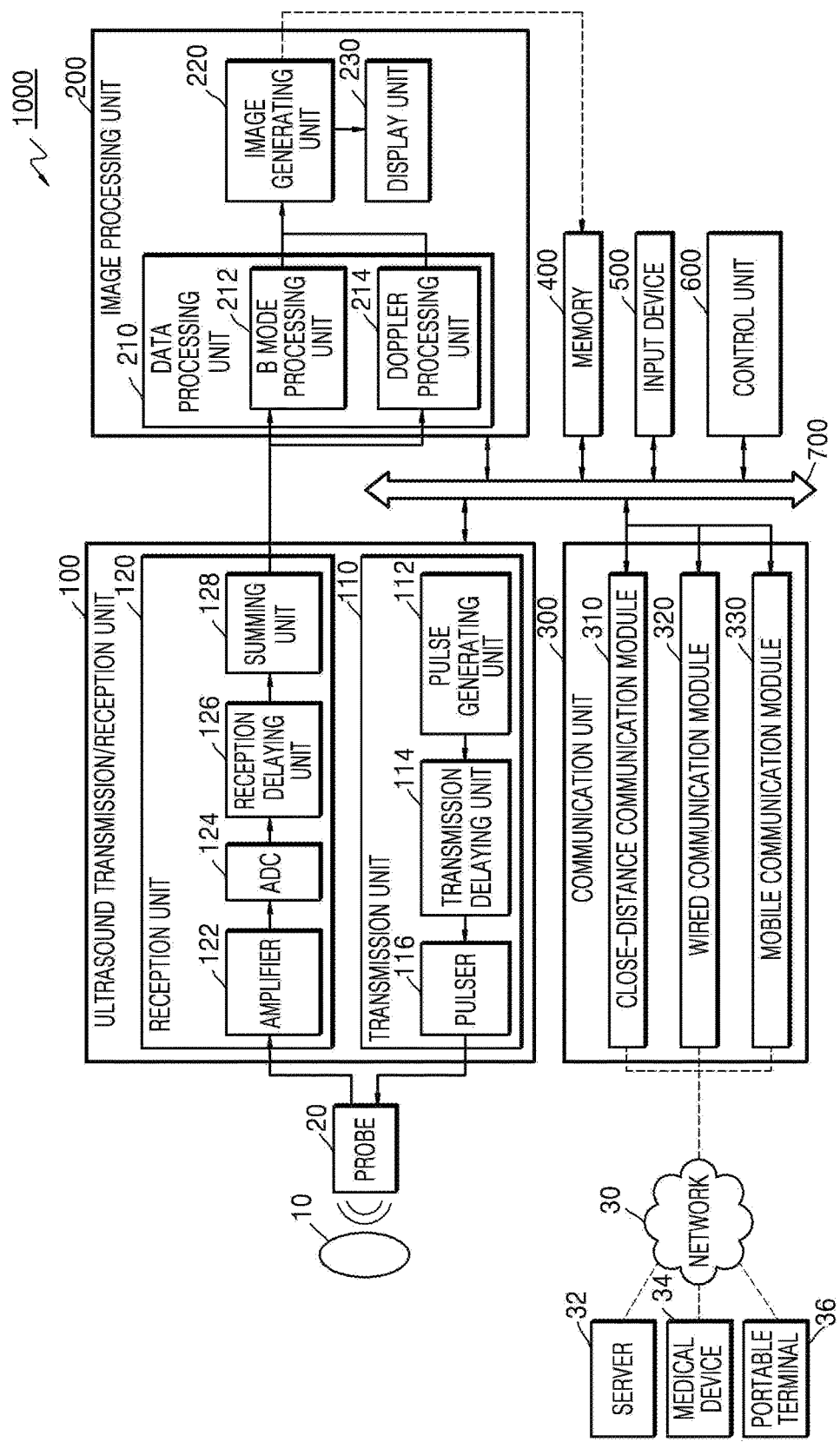
FIG. 1 is a block diagram showing a configuration of an ultrasound diagnosis apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

Throughout the specification, it will be understood that when an element is referred to as being "connected" to another element, it may be "directly connected" to the other element or "electrically connected" to the other element with intervening elements therebetween. It will be understood that when an element is referred to as being "connected to" another element, it may be "connected to" the other element via communication for transmitting and receiving information. It will be further understood that when a part "includes" or "comprises" an element, unless otherwise defined, the part may further include other elements, not excluding the other elements.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

An ultrasound diagnosis apparatus 1000 according to an embodiment may be configured as a block diagram of FIG. 1. However, FIG. 1 is illustrated for describing the configuration of the ultrasound diagnosis apparatus 1000. According to embodiments, the ultrasound diagnosis apparatus 1000 may further include configurations not shown in FIG. 1 or may omit some of the configurations illustrated in FIG. 1. Also, the configurations illustrated in FIG. 1 may be substituted by equivalents.

FIG. 1 is a block diagram showing a configuration of an ultrasound diagnosis apparatus 1000 according to an embodiment. Referring to FIG. 1, the ultrasound diagnosis apparatus 1000 may include a probe 20, an ultrasound transceiver 100, an image processor 200, a communication module 300, a display 300, a memory 400, an input device 500, and a controller 600, which may be connected to one another via buses 700.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 126. In some embodiments, the receiver 120 may not include the amplifier 122. In other words, if the sensitivity of the probe 20 or the capability of the ADC 124 to process bits is enhanced, the amplifier 122 may be omitted.

The image processor 200 generates an ultrasound image by scan-converting ultrasound data generated by the ultrasound transceiver 100 and displays the ultrasound image. However, according to embodiments, the scan-converting may be omitted. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 212 extracts B mode components from ultrasound data and processes the B mode components. An image generator 220 may generate an ultrasound image indicating signal intensities as brightness based on the extracted B mode components 212.

Similarly, a Doppler processor 214 may extract Doppler components from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the memory 400.

A display 230 displays the generated ultrasound image. The display 230 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 230 according to embodiments.

The communication module 300 is connected to a network 30 by wire or wirelessly to communicate with an external device or a server. The communication module 300 may exchange data with a hospital server or another medical apparatus in a hospital, which is connected thereto via a PACS. Furthermore, the communication module 300 may perform data communication according to the digital imaging and communications in medicine (DICOM) standard.

The communication module 300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 300 may receive information about a diagnosis history or medical treatment schedule of a patient from a server and utilizes the received information to diagnose the patient. Furthermore, the communication module 300 may perform data communication not only with a server or a medical apparatus in a hospital, but also with a portable terminal of a medical doctor or patient.

The communication module 300 is connected to the network 30 by wire or wirelessly to exchange data with a server 32, a medical apparatus 34, or a portable terminal 36. The communication module 300 may include one or more components for communication with external devices. For example, the communication module 1300 may include a local area communication module 310, a wired communication module 320, and a mobile communication module 330.

The local area communication module 310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 320 refers to a module for communication using electric signals or optical signals. Examples of wired communication techniques according to an embodiment may include communication via a twisted pair cable, a coaxial cable, an optical fiber cable, and an Ethernet cable.

The mobile communication module 330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 400 stores various data processed by the ultrasound diagnosis apparatus 1000. For example, the memory 400 may store medical data related to diagnosis of an object, such as ultrasound data and an ultrasound image that are input or output, and may also store algorithms or programs which are to be executed in the ultrasound diagnosis apparatus 1000.

The memory 400 may be any of various storage media, e.g., a flash memory, a hard disk drive, EEPROM, etc. Furthermore, the ultrasound diagnosis apparatus 1000 may utilize web storage or a cloud server that performs the storage function of the memory 400 online.

The input device 500 refers to a means via which a user inputs data for controlling the ultrasound diagnosis apparatus 1000. The input device 500 may include hardware components, such as a keypad, a mouse, a touch panel, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 600 may control all operations of the ultrasound diagnosis apparatus 1000. In other words, the controller 600 may control operations among the probe 20, the ultrasound transceiver 100, the image processor 200, the communication module 300, the memory 400, and the input device 500 shown in FIG. 1.

All or some of the probe 20, the ultrasound transceiver 100, the image processor 200, the communication module 300, the memory 400, the input device 500, and the controller 600 may be implemented as software modules. However, embodiments are not limited thereto, and some of the components stated above may be implemented as hardware modules. Furthermore, at least one selected from the ultrasound transceiver 100, the image processor 200, and the communication module 300 may be included in the controller 600. However, embodiments of the present invention are not limited thereto.

Figure 2:
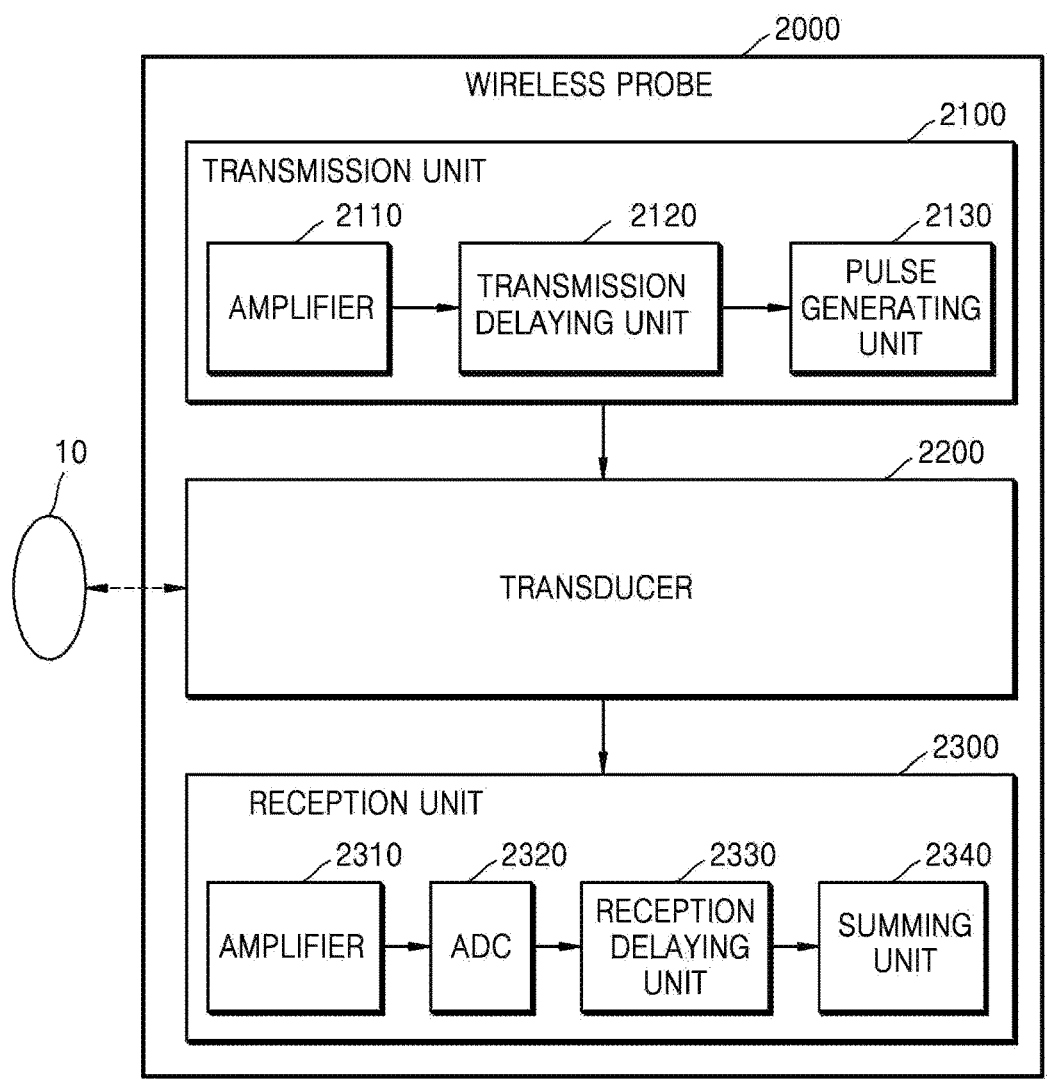
FIG. 2 is a block diagram showing a configuration of a wireless probe according to an embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

Figure 3:
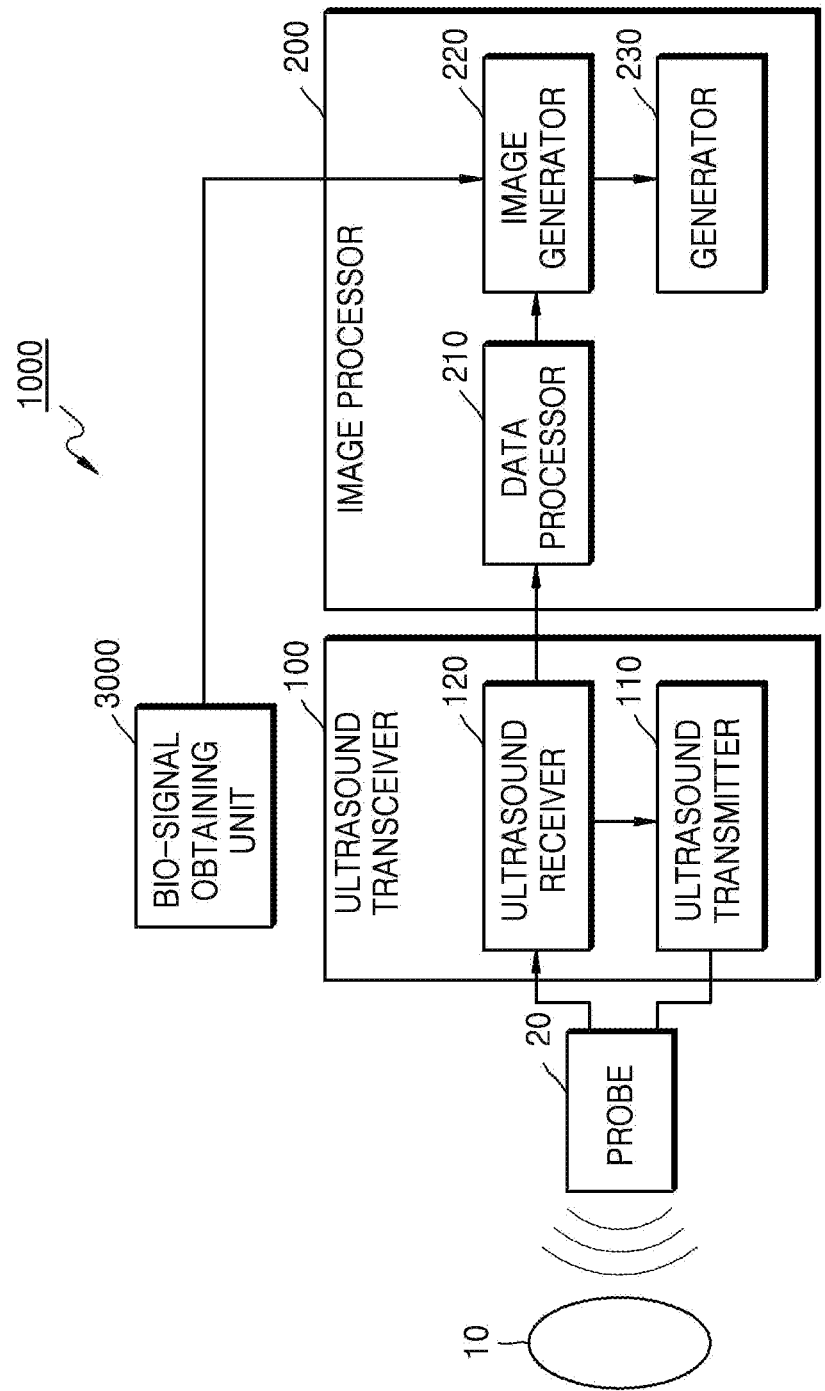
FIG. 3 is a block diagram showing a configuration of an ultrasound diagnosis apparatus according to an embodiment.

FIG. 3 is a block diagram of a configuration of the ultrasound diagnosis apparatus 1000.

The ultrasound diagnosis apparatus 1000 may include the ultrasound transceiver 100, the image processor 200, and a bio-signal obtaining unit 3000. The ultrasound transceiver 100 may include the transmitter 110 (that is, the ultrasound transmitter) and the receiver 120 (that is, the ultrasound receiver). The image processor 200 may include the data processor 210 and the image generator 220.

The transmitter 110 may supply a driving signal to the probe 20. When a pulse generated by the transmitter 110 is transmitted to the probe 20, the probe 20 may transmit ultrasound waves to an object. Also, the receiver 120 may generate ultrasound data (that is, reception signals) by processing echo signals (that is, reflection waves) received from the probe 20.

The image processor 200 may generate an ultrasound image by scan-converting ultrasound data generated by the ultrasound transceiver 100. The data processor 210 may obtain first loop image data and second loop image data, based on the ultrasound data (that is, the reception signals) generated by the receiver 120. Here, the loop image data may refer to data that is extracted from the ultrasound data in order to generate a loop image, such as a Doppler image or an M mode image. For example, when the image that is to be generated is the Doppler image, the first loop image data and the second loop image data may be a Doppler spectrum extracted from the ultrasound data. Also, the first loop image data and the second loop image data may be data generated from the ultrasound data that are obtained at different points in time. Alternatively, the first loop image data and the second loop image data may be data generated from the ultrasound data with respect to different parts of an object.

The image generator 220 may generate combined data that combines the first loop image data and the second loop image data. Here, the image generator 220 may combine the first loop image data and the second loop image data based on bio-signals obtained by the bio-signal obtaining unit 3000. For example, the image generator 220 may determine a location of a characteristic point in the first loop image data based on the bio-signals. Also, the image generator 220 may determine a location of a characteristic point in the second loop image data based on the bio-signals. The image generator 220 may combine the first loop image data and the second loop image data so that the location of the characteristic point in the first loop image data and the location of the characteristic point in the second loop image data correspond to each other. The image generator 220 may expand, reduce, change the location of, or flip at least one of the first loop image data and the second loop image data, in order to combine the first loop image data and the second loop image data. However, it is not limited thereto. To make the locations of the characteristic points correspond to each other may be referred to as "to synchronize" the locations of the characteristic points.

The bio-signal obtaining unit 3000 may be realized as various types according to embodiments. For example, when the bio-signal is the electrocardiography (ECG), the bio-signal obtaining unit 3000 may include a sensor (not shown) for detecting the ECG. In this case, the bio-signal obtaining unit 3000 may obtain ECG signals via the sensor. According to another example, the bio-signal obtaining unit 3000 may include the communication module 300. In this case, information with respect to the ECG signals may be received from an external ECG measuring device. However, it is not limited thereto.

Also, the image processor 200 of the ultrasound diagnosis apparatus 1000 may further include the display 230 that is configured to display the combined data. The display 230 displays the combined data, thereby displaying the first loop image data and the second loop image data on one screen. A user may more easily recognize data information through the first loop image data and the second loop image data that are synchronized. For example, when the first loop image data is blood flow Doppler image data indicating a blood flow, and the second loop image data is a tissue Doppler image indicating a heart muscle motion, the user may easily determine a heart cycle by using the combined data which simultaneously indicates the first loop image data and the second loop image data.

Figure 4:
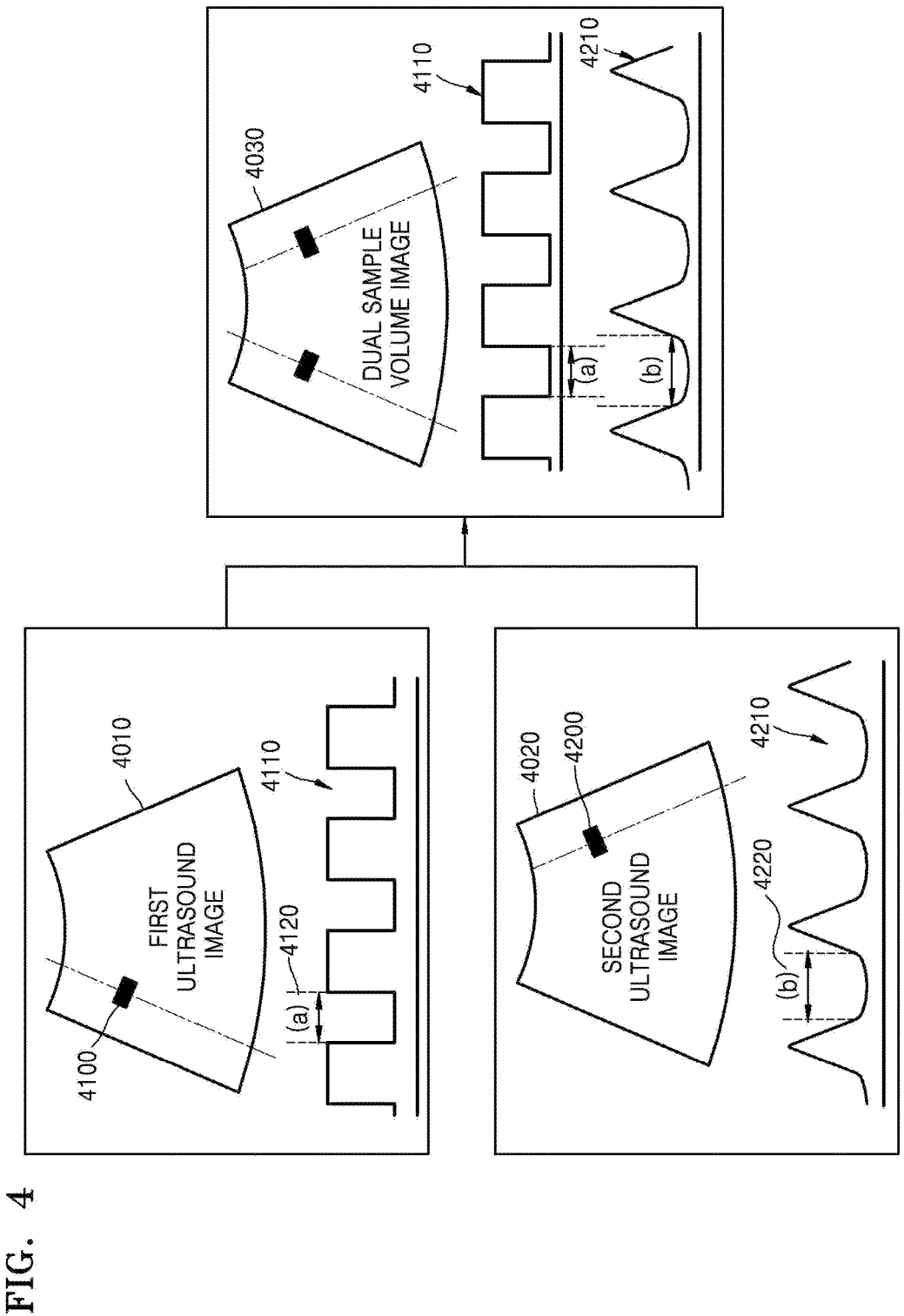
FIG. 4 is a view showing an image displayed by an ultrasound diagnosis apparatus according to an embodiment.

FIG. 4 is a view of an image displayed by the ultrasound diagnosis apparatus 1000.

The ultrasound diagnosis apparatus 1000 may display first loop image data 4110 corresponding to a first location 4100 on a first ultrasound image 4010 and second loop image data 4210 corresponding to a second location 4200 on a second ultrasound image 4020. A user may sometimes have to compare a portion 4120 of the first loop image data 4110 and a portion 4220 of the second loop image data 4220. For example, in order to measure the myocardial performance index (the Tei index), a portion (a) 4120 and a portion (b) 4220 may have to be compared. The Tei index, which is a predictor that may be used for evaluating overall ventricular functions, may be used as an index with respect to an evaluation of overall heart functions of a congestive heart failure patient. In this case, the ultrasound diagnosis apparatus 1000 may display the first loop image data 4110 and the second loop image data 4210 together with a dual sample volume image, as illustrated in FIG. 4. However, when the ultrasound diagnosis apparatus 1000 displays the first loop image data 4110 and the second loop image data 4210 as illustrated in FIG. 4, it may be difficult for the user to instantly compare the portion 4120 of the first loop image data 4110 and the portion 4220 of the second loop image data 4210.

Throughout the specification, the description is made by focusing on the embodiment in which two pieces of loop image data (that is, the first loop image data and the second loop image data) are combined. However, the present inventive concept includes the case in which three or more pieces of loop image data are combined.

Figure 5:
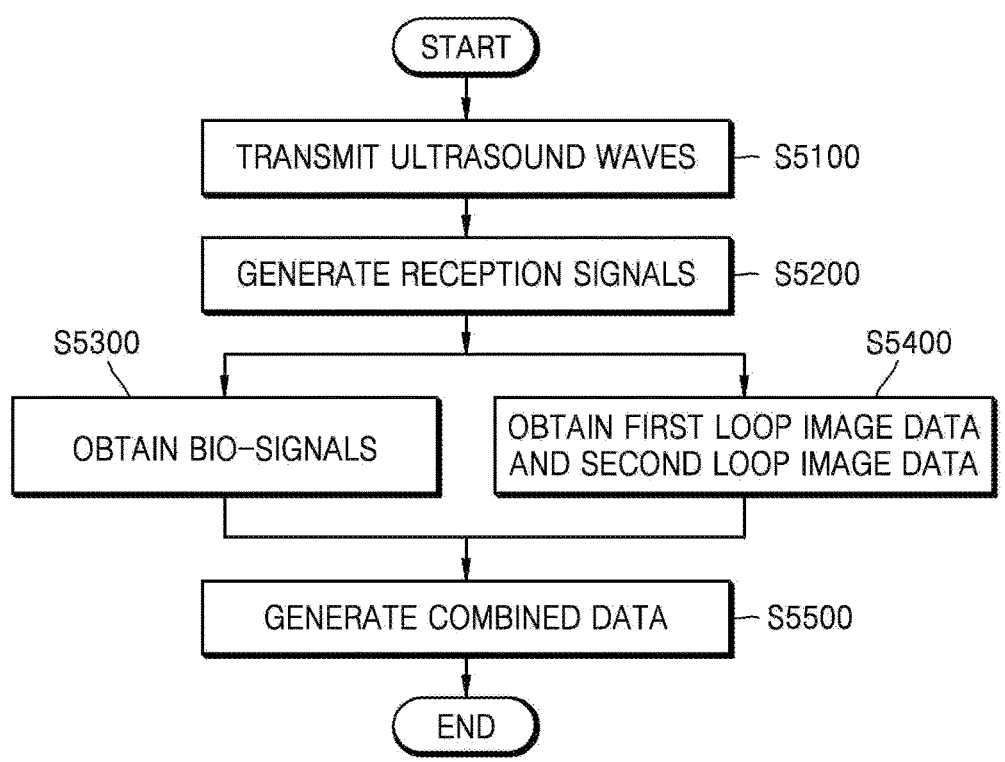
FIG. 5 is a flowchart of an ultrasound diagnosis method according to an embodiment.

FIG. 5 is a flowchart of an ultrasound diagnosis method according to an embodiment.

The ultrasound diagnosis apparatus 1000 may transmit ultrasound waves to the object 10 by using the probe 20 in operation S5100. Then, the ultrasound diagnosis apparatus 1000 may receive echo signals which are reflection waves of the transmitted ultrasound waves, via the probe 20. The ultrasound diagnosis apparatus 1000 may generate ultrasound data (that is, reception signals) based on the echo signals, in operation S5200.

Also, the ultrasound diagnosis apparatus 1000 may obtain bio-signals. The bio-signals are electrical or chemical signals generated by a living body, and may denote signals which may be sensed via a sensor. In some embodiments, the bio-signals may be signals which are periodically repeated, such as the ECG. However, the bio-signals are not limited thereto. There may be various types of methods of obtaining the bio-signals, according to embodiments.

The ultrasound diagnosis apparatus 1000 may obtain first loop image data and second loop image data based on the reception signals generated in operation S5200, in operation S5400. The loop image data may include data that is extracted from the ultrasound data in order to generate a loop image, such as a Doppler image or an M mode image. For example, the first loop image data and the second loop image data may be a Doppler spectrum extracted from the ultrasound data. Also, the first loop image data and the second loop image data may be data generated from the ultrasound data obtained at different points in time. Alternatively, the first loop image data and the second loop image data may be data generated from the ultrasound data with respect to different parts of an object.

Next, the ultrasound diagnosis apparatus 1000 may combine the first loop image data and the second loop image data in operation S5400, based on bio-signals obtained in operation S5300. That is, the ultrasound diagnosis apparatus 1000 may synchronize the first loop image data and the second loop image data based on the bio-signals. The ultrasound diagnosis apparatus 1000 may generate combined data that combines the first loop image data and the second loop image data, in operation S5500.

Figure 6:
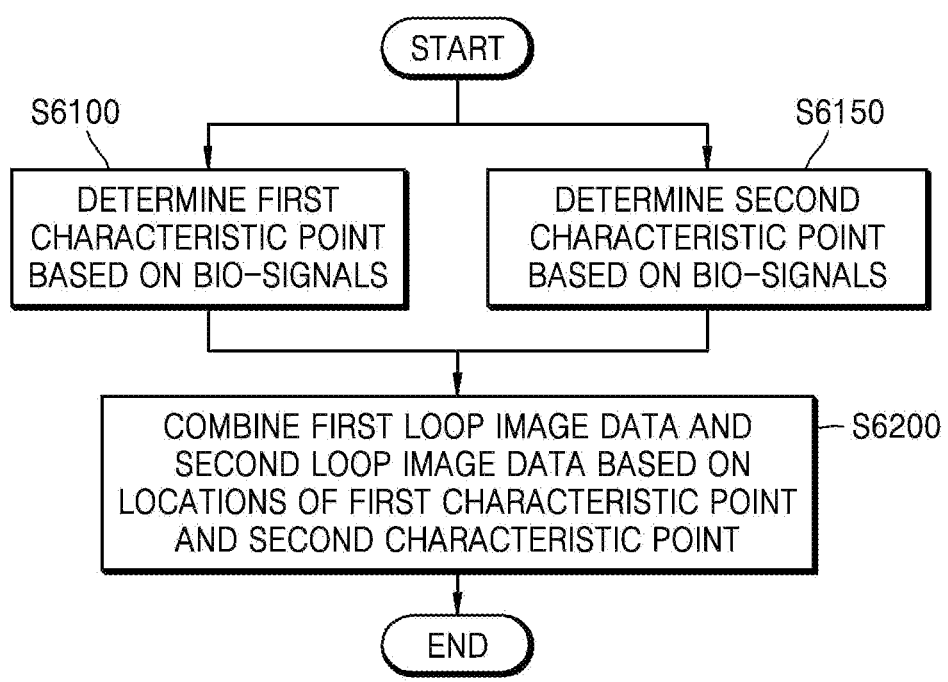
FIG. 6 is a flowchart of a process of generating combined data, according to an embodiment.

FIG. 6 is a flowchart of a process of generating combined data, according to an embodiment.

First, the ultrasound diagnosis apparatus 1000 may determine a first characteristic point in first loop image data, based on bio-signals, in operation S6100. Also, the ultrasound diagnosis apparatus 1000 may determine a first characteristic point in second loop image data, based on the bio-signals, in operation S6150.

Figure 7:
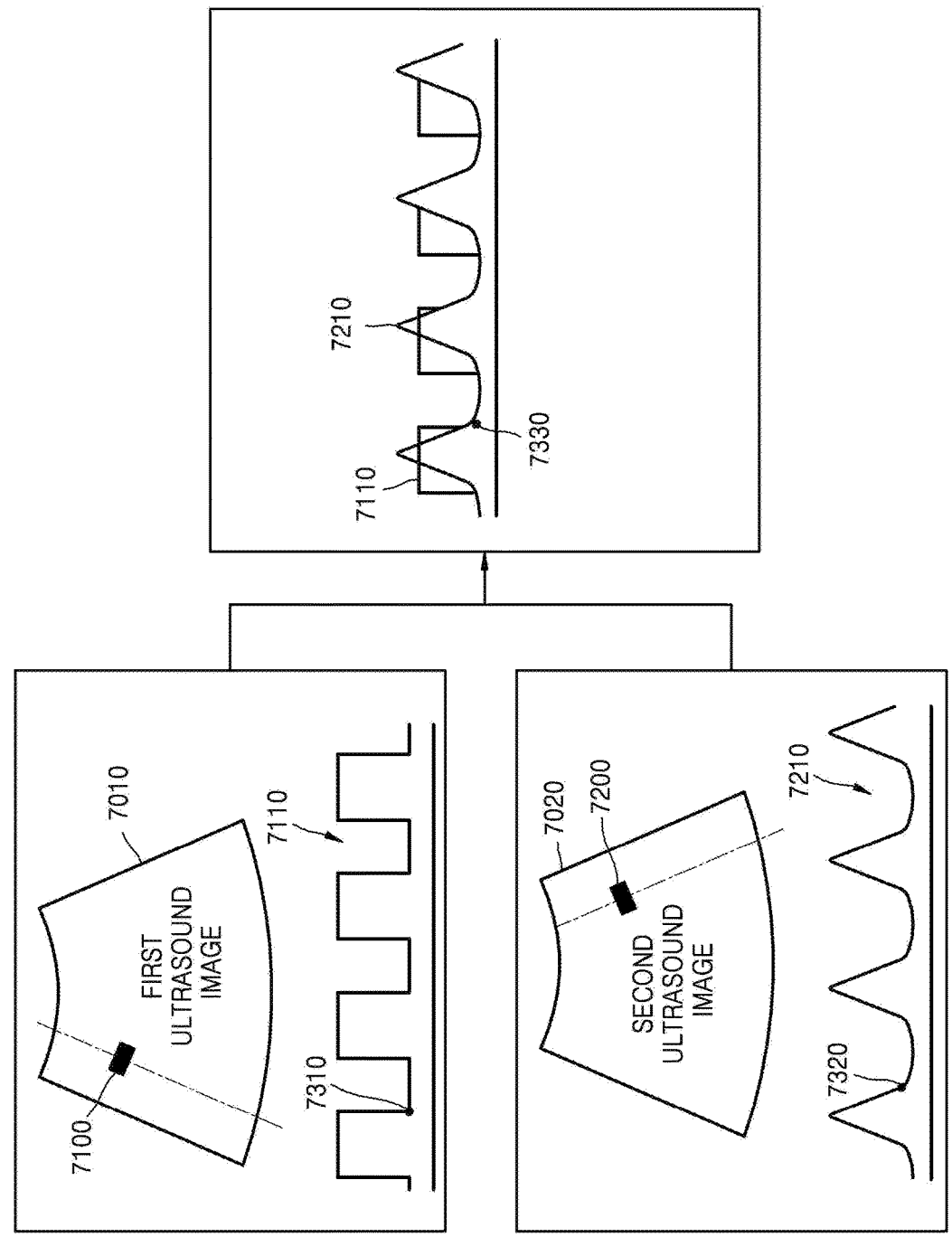
FIG. 7 is a view of a method of displaying first loop image data and second loop image data according to a first embodiment.

FIG. 7 is a view of a method of displaying first loop image data 7110 and second loop image data 7210, according to a first embodiment.

According to the first embodiment, the ultrasound diagnosis apparatus 1000 may obtain the first loop image data 7110 corresponding to a first location 7100 on a first ultrasound image 7010. Also, the ultrasound diagnosis apparatus 1000 may determine a first characteristic point 7310 in the first loop image data 7110, based on bio-signals.

Also, according to the first embodiment, the ultrasound diagnosis apparatus 1000 may obtain the second loop image data 7210 corresponding to a second location 7200 on a second ultrasound image 7020. Also, the ultrasound diagnosis apparatus 1000 may determine a second characteristic point 7320 in the second loop image data 7210 based on the bio-signals.

Then, the ultrasound diagnosis apparatus 1000 may combine the first loop image data 7110 and the second loop image data 7210 so that the first characteristic point 7310 and the second characteristic point 7320 are located at one point 7330. Here, the ultrasound diagnosis apparatus 1000 may determine an overlap relation between the first loop image data 7110 and the second loop image data 7210. For example, referring to FIG. 7, it may be configured such that the second loop image 7210 may be displayed in front of the first loop image data 7110.

Figure 8:
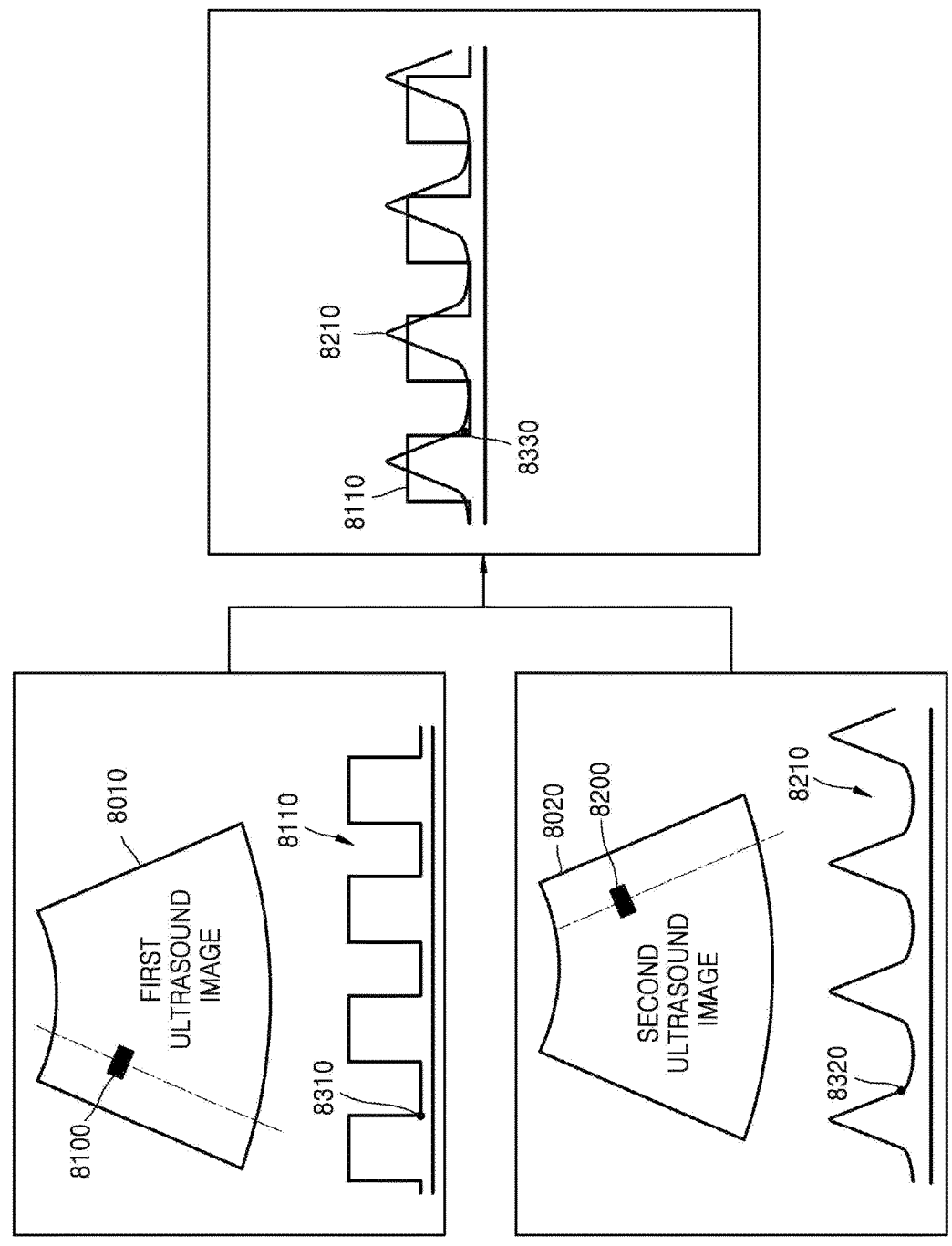
FIG. 8 is a view of a method of displaying first loop image data and second loop image data according to a second embodiment.

FIG. 8 is a view of a method of displaying first loop image data 8110 and second loop image data 8210 according to a second embodiment.

According to the second embodiment, the ultrasound diagnosis apparatus 1000 may obtain the first loop image data 8110 corresponding to a first location 8100 on a first ultrasound image 8010. Also, the ultrasound diagnosis apparatus 1000 may determine a first characteristic point 8310 in the first loop image data 8110 based on bio-signals.

Also, according to the second embodiment, the ultrasound diagnosis apparatus 1000 may obtain the second loop image data 8210 corresponding to a second location 8200 on a second ultrasound image 8020. Also, the ultrasound diagnosis apparatus 1000 may determine a second characteristic point 8320 in the second loop image data 8210 based on the bio-signals.

Then, the ultrasound diagnosis apparatus 1000 may combine the first loop image data 8110 and the second loop image data 8210 so that the first characteristic point 8310 and the second characteristic point 8320 are located at one point 8330. Here, the ultrasound diagnosis apparatus 1000 may determine a transparency in which the first loop image data 8110 and the second loop image data 8210 are to be displayed. By controlling the transparency of at least one of the first loop image data 8110 and the second loop image data 8210, the ultrasound diagnosis apparatus 1000 may make the first loop image data 8110 and the second loop image data 8210 seen overlapped.

Figure 9:
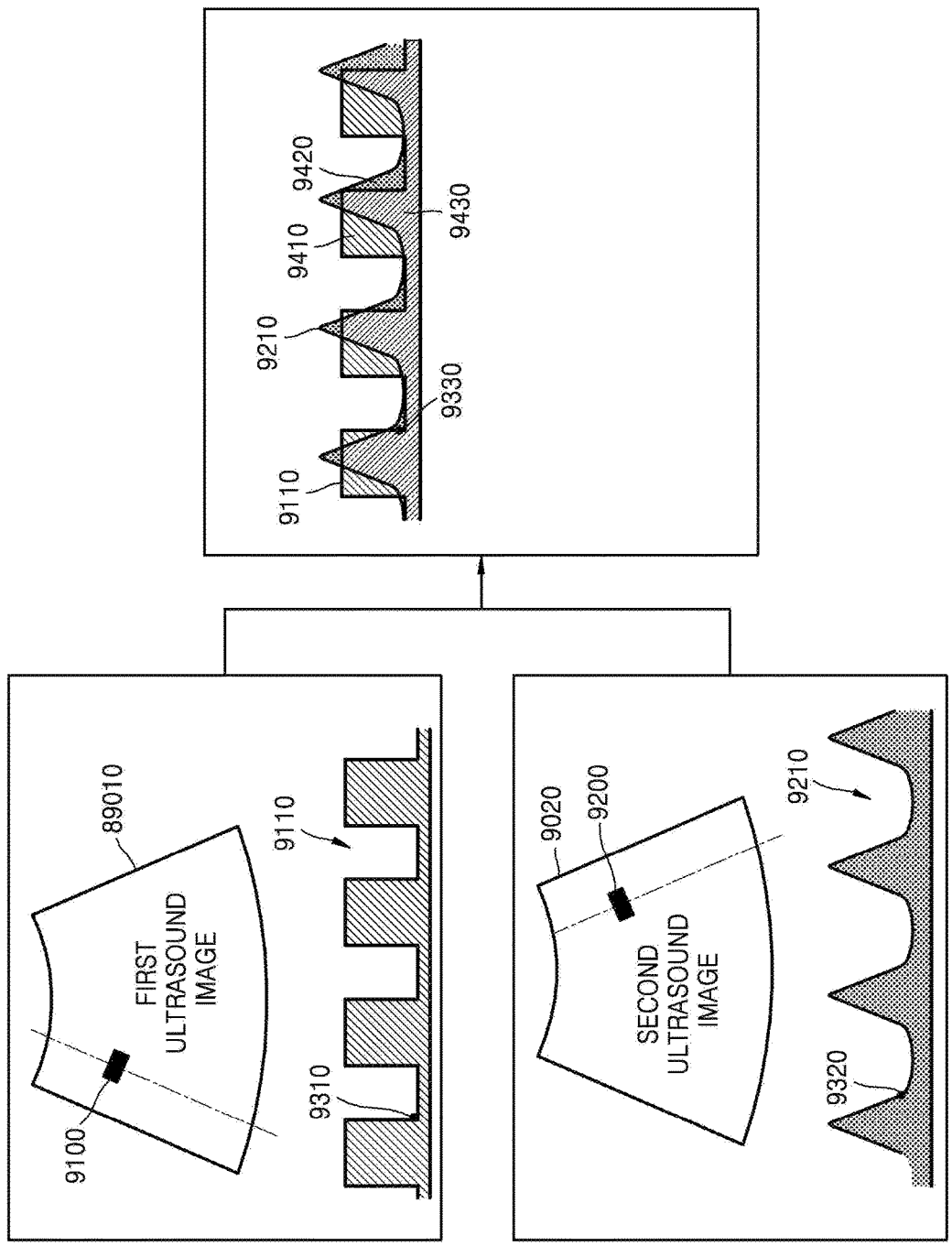
FIG. 9 is a view of a method of displaying first loop image data and second loop image data according to a third embodiment.

FIG. 9 is a view of a method of displaying first loop image data 9110 and second loop image data 9210 according to a third embodiment.

According to the third embodiment, the ultrasound diagnosis apparatus 1000 may obtain the first loop image data 9110 corresponding to a first location 9100 on a first ultrasound image 9010. Also, the ultrasound diagnosis apparatus 1000 may determine a first characteristic point 9310 in the first loop image data 9110 based on bio-signals.

Also, according to the third embodiment, the ultrasound diagnosis apparatus 1000 may obtain the second loop image data 9210 corresponding to a second location 9200 on a second ultrasound image 9020. Also, the ultrasound diagnosis apparatus 1000 may determine a second characteristic point 9320 in the second loop image data 9210 based on the bio-signals.

Then, the ultrasound diagnosis apparatus 1000 may combine the first loop image data 9110 and the second loop image data 9210 so that the first characteristic point 9310 and the second characteristic point 9320 are located at one point 9330. Here, the image generator 220 of the ultrasound diagnosis apparatus 1000 may configure a color map with respect to combined data that combines the first loop image data 9110 and the second loop image data 9210. For example, referring to FIG. 9, the image generator 220 may configure the color map with respect to the combined data such that a portion 9410 in which only the first loop image data 9110 is displayed is displayed in a red color, and a portion 9420 in which only the second loop image data 9210 is displayed is displayed in a blue color. Also, the color map with respect to the combined data may be configured such that a portion 9430 in which the first loop image data 9110 and the second loop image data 9210 are displayed in an overlapped manner is displayed in a violet color.

Figure 10:
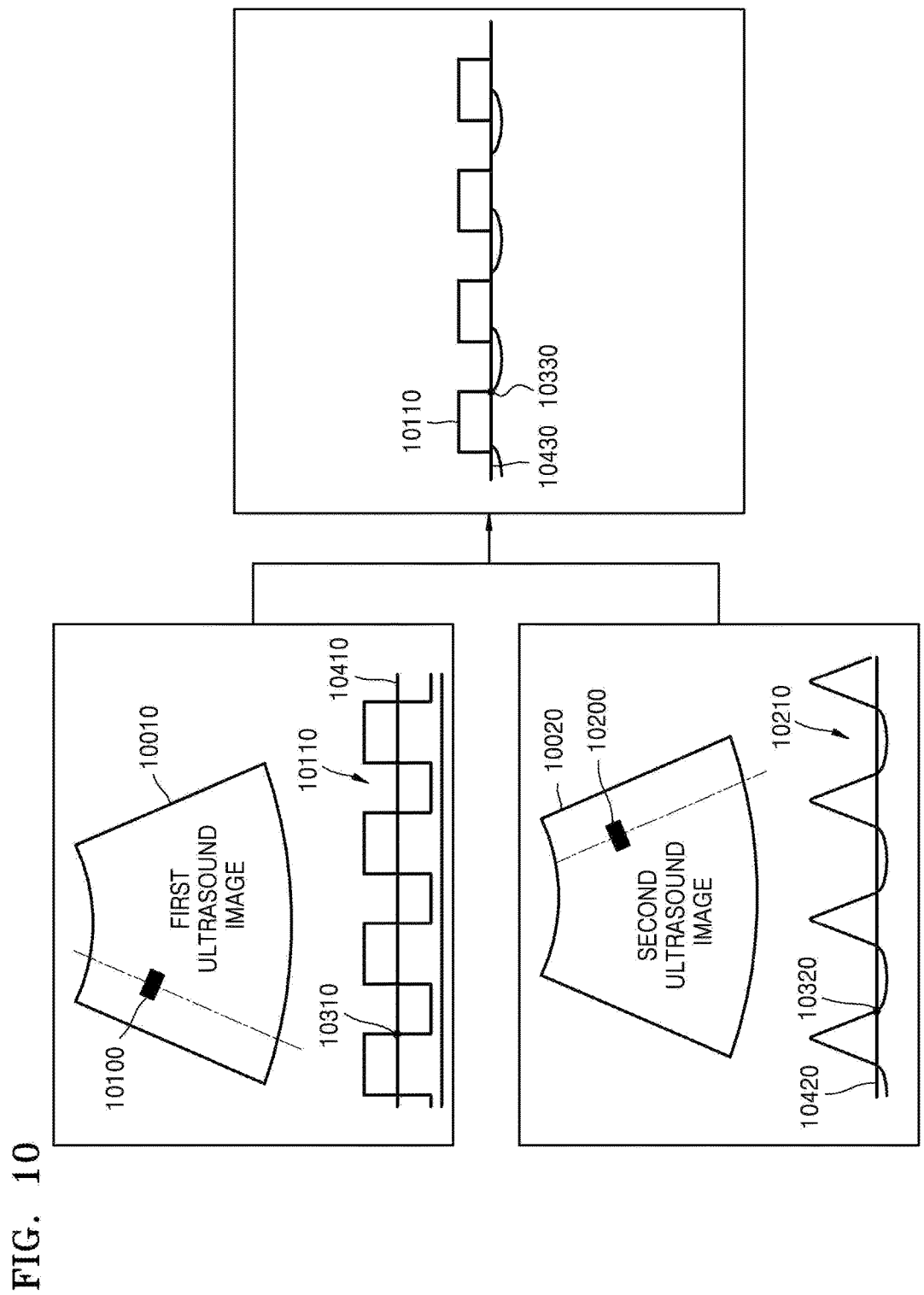
FIG. 10 is a view of a method of displaying first loop image data and second loop image data according to a fourth embodiment.

FIG. 10 is a view of a method of displaying first loop image data 10110 and second loop image data 10210 according to a fourth embodiment.

According to the fourth embodiment, the ultrasound diagnosis apparatus 1000 may obtain the first loop image data 10110 corresponding to a first location 10100 on a first ultrasound image 10010. Also, the ultrasound diagnosis apparatus 1000 may determine a first characteristic point 10310 in the first loop image data 10110 based on bio-signals.

Also, according to the fourth embodiment, the ultrasound diagnosis apparatus 1000 may obtain the second loop image data 10210 corresponding to a second location 10200 on a second ultrasound image 10020. Also, the ultrasound diagnosis apparatus 1000 may determine a second characteristic point 10320 in the second loop image data 10210 based on the bio-signals.

Then, the ultrasound diagnosis apparatus 1000 may combine the first loop image data 10110 and the second loop image data 10210 so that the first characteristic point 10310 and the second characteristic point 10320 are located at one point 10330. Here, the image generator 220 of the ultrasound diagnosis apparatus 1000 may generate combined data that combines a portion of the first loop image data 10110 and a portion of the second loop image data 10210. Referring to FIG. 10, the combined data may include only data having a value that is equal to or higher than a reference level 10410 from among the first loop image data 10110. Also, the combined data may include only data having a value that is lower than a reference level 10420 from among the second loop image data 10210. In some embodiments, a location of at least the portion of the first loop image data 10110 included in the combined data and a location of at least the portion of the second loop image data 10210 included in the combined data may be exchanged. That is, the combined data may include data having a value that is lower than the reference level 10410 from among the first loop image data 10110 and data having a value that is equal to or higher than the reference level 10420 from among the second loop image data 10210.

Also, in some embodiments, in order not to overlap the first loop image data 10110 and the second loop image data 10210, the image generator 220 may flip the second loop image data 10210 upside down. That is, the combined data may include at least a portion of the first loop image data 10110 and at least a portion of the second loop image data 10210. The first image data 10110 includes data having the value that is equal to or higher than the reference level 10410 from among the first loop image data 10110. The second loop image data 10210 includes data which is flipped data having the value that is equal to or higher than the reference level 10420 from among the second loop image 10210.

The embodiments are not independent from one another, and the present inventive concept may be realized by combining a plurality of embodiments. For example, the image generator 220 may configure the color map with respect to each of the first loop image data and the second loop image data, and may at the same time control the transparency of each of the first loop image data and the second loop image data.

Figure 11:
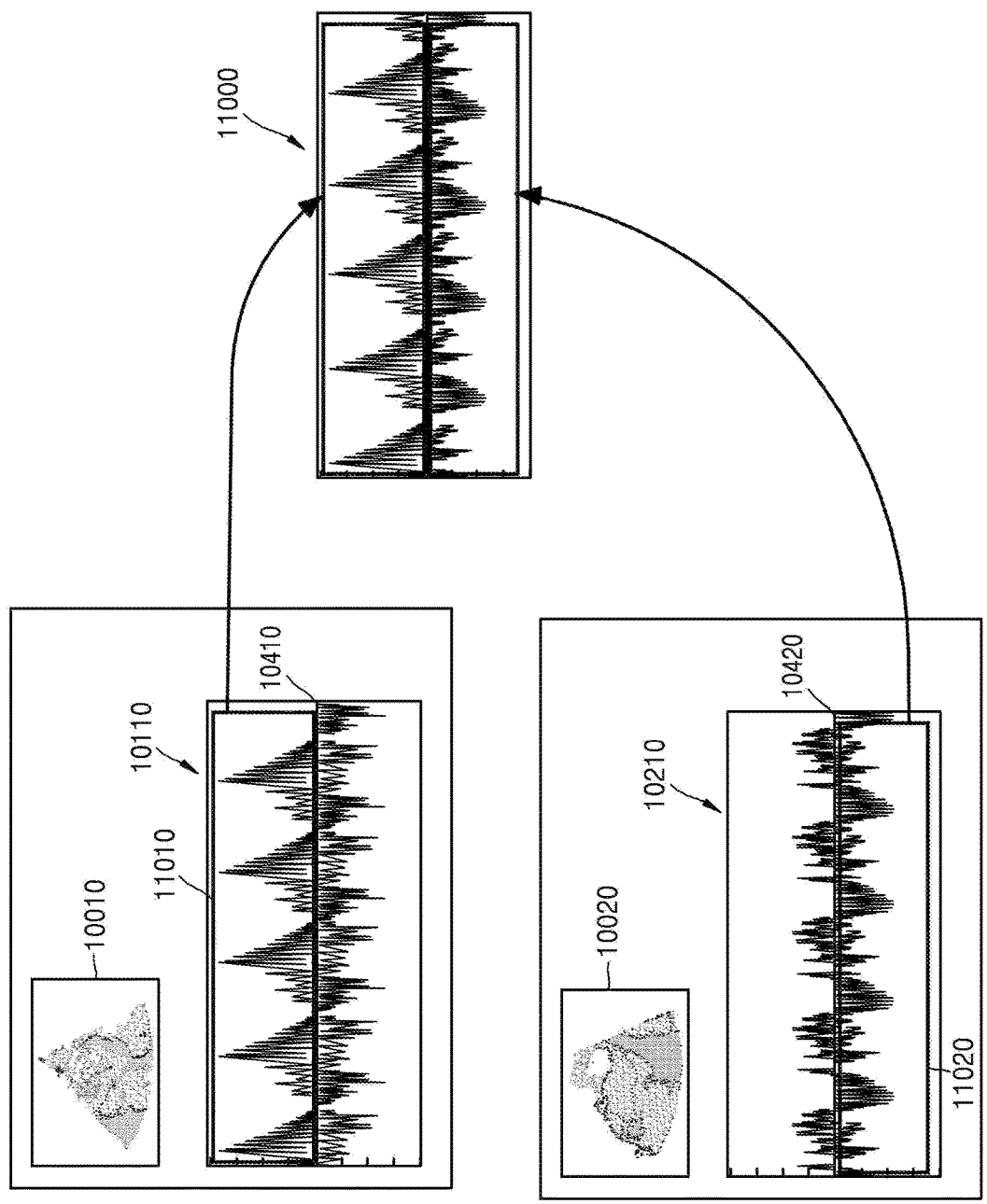
FIG. 11 is a view of first loop image data, second loop image data, and combined data according to a fourth embodiment.

FIG. 11 is a view of the first loop image data 10110, the second loop image data 10210, and the combined data according to the fourth embodiment.

Referring to FIG. 11, the ultrasound diagnosis apparatus 1000 may obtain data 11010 having a value that is higher than the reference level 10410 from among the first loop image data 10110 related to the first ultrasound image 10010. Also, the ultrasound diagnosis apparatus 1000 may obtain data 11020 having a value that is equal to or lower than the reference level 10420.

The ultrasound diagnosis apparatus 1000 may generate combined data 11000 that combines the data 11010 and the data 11020.

The one or more embodiments may be embodied as a recording medium, e.g., a program module to be executed in computers, which include computer-readable commands. A computer-readable recording medium may be an arbitrary available medium accessible by a computer, and examples thereof include all volatile and non-volatile media and separable and non-separable media. Further, examples of the computer-readable recording medium may include a computer storage medium and a communication medium. Examples of the computer storage medium include all volatile and non-volatile media and separable and non-separable medial, which have been implemented by an arbitrary method or technology, for storing information such as computer-readable commands, data structures, program modules, and other data. The communication medium typically includes a computer-readable command, a data structure, a program module, other data of a modulated data signal, or another transmission mechanism, and an example thereof includes an arbitrary information transmission medium.

Also, the one or more embodiments may be written as computer programs and can be implemented in general-use digital computers that execute the programs using a computer readable recording medium.

While one or more exemplary embodiments have been particularly shown and described with reference to exemplary embodiments thereof, it will be understood by one of ordinary skill in the art that various changes in form and details may be made herein without departing from the spirit and scope of the present invention as defined by the following claims. Hence, it will be understood that the embodiments described above are not limiting of the scope of the invention. For example, each component described in a single type may be executed in a distributed manner, and components described distributed may also be executed in an integrated form.

What is claimed is:

1. An ultrasound diagnosis apparatus comprising:
a probe;
an ultrasound transmitter configured to transmit ultrasound waves to an object by using the probe;
an ultrasound receiver configured to generate ultrasound data based on reflection waves corresponding to the transmitted ultrasound waves;
a bio-signal obtaining unit configured to obtain bio-signals that are periodically generated;
a data processor configured to obtain first loop image data and second loop image data based on the ultrasound data; and
an image generator configured to:
determine a first characteristic point in the first loop image data, based on the bio-signals;
determine a second characteristic point corresponding to the first characteristic point, in the second loop image data, based on the bio-signals; and
generate combined data by combining the first loop image data and the second loop data, image based on a location of the first characteristic point and a location of the second characteristic point.

2. The ultrasound diagnosis apparatus of claim 1, wherein the combined data generated by the image generator comprises only data having a value that is equal to or higher than a reference level or only data having a value that is lower than the reference level, from among the first loop image data and the second loop image data.

3. The ultrasound diagnosis apparatus of claim 2, wherein the image generator obtains the data having a value that is equal to or higher than the reference level from among the first loop image data and obtains the data having a value that is lower than the reference level from among the second loop image data, and
the combined data is a combination of the data having the value that is equal to or higher than the reference level and obtained from among the first loop image data and the data having the value that is lower than the reference level and obtained from among the second loop image data.

4. The ultrasound diagnosis apparatus of claim 1, further comprising a display configured to display the first loop image data and the second loop image data simultaneously on a screen based on the combined data.

5. The ultrasound diagnosis apparatus of claim 4, wherein the image generator configures a color map with respect to each of the first loop image data and the second loop image data, and
the display displays the first loop image data and the second loop image data based on the configuration of the color map.

6. The ultrasound diagnosis apparatus of claim 5, wherein the image generator determines at least one selected from a transparency, a sequential relationship, and the configuration of the color map, with respect to each of the first loop image data and the second loop image data.

7. The ultrasound diagnosis apparatus of claim 1, wherein the bio-signals comprise electrocardiogram (ECG) information with respect to the object.

8. The ultrasound diagnosis apparatus of claim 1, wherein the first loop image data and the second loop image data comprises at least one selected from Doppler spectrum data and M mode image data.

9. An ultrasound diagnosis method comprising:
transmitting ultrasound waves to an object by using a probe;
generating ultrasound data based on reflection waves corresponding to the transmitted ultrasound waves;
obtaining bio-signals that are periodically generated;
obtaining first loop image data and second loop image data based on the ultrasound data;
determining a first characteristic point in the first loop image data, based on the bio-signals;
determining a second characteristic point corresponding to the first characteristic point, in the second loop image data, based on the bio-signals; and
generating combined data by combining the first loop image data and the second loop image data based on a location of the first characteristic point and a location of the second characteristic point.

10. The ultrasound diagnosis method of claim 9, wherein the combined data comprises only data having a value that is equal to or higher than a reference level or only data having a value that is equal to or lower than a reference level, from among the first loop image data and the second loop image data.

11. The ultrasound diagnosis method of claim 10, wherein the generating of the combined data comprises:
obtaining the data having a value that is equal to or higher than the reference level from among the first loop image data;
obtaining the data having a value that is lower than the reference level from among the second loop image data; and
generating the combined data by combining the data having the value that is equal to or higher than the reference level from among the first loop image data and the data having the value that is lower than the reference level from among the second loop image data.

12. The ultrasound diagnosis method of claim 9, further comprising displaying the first loop image data and the second loop image data simultaneously on a screen based on the combined data.

13. The ultrasound diagnosis method of claim 12, wherein the generating of the combined data comprises configuring a color map with respect to each of the first loop image data and the second loop image data, and
the displaying of the first loop image data and the second loop image data comprises displaying the first loop image data and the second loop image data based on the configuration of the color map.

14. The ultrasound diagnosis method of claim 13, wherein the generating of the combined data comprises determining at least one selected from a transparency, a sequential relationship, and the configuration of the color map, with respect to each of the first loop image data and the second loop image data.

15. The ultrasound diagnosis method of claim 9, wherein the obtaining of the bio-signals comprises obtaining electrocardiogram (ECG) information with respect to the object.

16. The ultrasound diagnosis method of claim 9, wherein the first loop image data and the second loop image data comprises at least one selected from Doppler spectrum data and M mode image data.

17. A non-transitory computer-readable recording medium having embodied thereon a computer program for executing the method of claim 9.

* * * * *